(12) United States Patent
de Carvalho

(10) Patent No.: US 6,464,675 B2
(45) Date of Patent: Oct. 15, 2002

(54) SANITARY NAPKIN

(75) Inventor: Antonio Carlos Ribeiro de Carvalho, Sao Paulo (BR)

(73) Assignee: Johnson & Johnson Industria e Comercio LTDA (BR)

( * ) Notice: Subject to any disclaimer, the term of this patent is extended or adjusted under 35 U.S.C. 154(b) by 0 days.

(21) Appl. No.: 09/740,111

(22) Filed: Dec. 19, 2000

(65) Prior Publication Data

US 2002/0077619 A1 Jun. 20, 2002

(51) Int. Cl.[7] ................................................ A61F 13/15
(52) U.S. Cl. ............. 604/385.04; 604/387; 604/385.01; 604/386; 604/389; 604/358
(58) Field of Search ............................ 604/385.04, 387, 604/385.01, 386, 389, 358

(56) References Cited

U.S. PATENT DOCUMENTS 5,354,400 A * 10/1994 Lavash ........................ 156/227
5,383,867 A * 1/1995 Klinger ................. 604/385.01

FOREIGN PATENT DOCUMENTS

WO        WO 01/72252 A1        10/2001

* cited by examiner

Primary Examiner—Rodney M. Lindsey
Assistant Examiner—Angela J Grayson

(57) ABSTRACT

A sanitary napkin is described, which includes a substantially planar and elongate body defining two larger longitudinal side edges. The body is provided with a garment faceable outer layer of liquid impermeable material, a body faceable cover layer of liquid permeable material, an absorbent core inserted into the body between the outer layer and the cover layer, and at least one substantially protuberant flexible flap substantially projecting outwards from each longitudinal side edge of the body, the flap being substantially transparent and/or translucent.

2 Claims, 2 Drawing Sheets

SANITARY NAPKIN

FIELD OF INVENTION

The present invention relates to absorbent articles adapted to be worn in an undergarment to absorb body fluids and include articles such as a sanitary napkin, panty liner or incontinence pad.

BACKGROUND OF THE INVENTION

Conventionally, sanitary napkins have two basic configurations, which are described below.

A first configuration comprises sanitary napkins without side flaps for additional fixation. Sanitary napkins without flaps are discreet and may be worn with bathing costumes, skirts, sports shorts or other women's garments, without other people noticing that the user is wearing the sanitary napkin. However, the lack of additional fixation provided by the side flaps may allow the napkin to move with respect to the undergarment of the wearer, which might cause discomfort and leakage of menstrual flow, a situation that brings special discomfort to the wearer.

This possibility of the sanitary napkin moving is especially critical when the woman is practicing sports or other activities that cause constant movement of her legs. The drawbacks cited above cause the sanitary napkins without flaps to have limited acceptance by the consumer market.

A second configuration comprises sanitary napkins provided with side flaps for additional fixation. Conventional sanitary napkins are formed of an opaque and/or non-transparent materials which mask the presence of any absorbed fluids such as blood. The flaps are flexible and adapted to be folded over the crotch portion of a user's undergarment in use. The flaps are generally provided with an adhesive on a garment faceable surface of the flaps, which brings about correct and safe fixation, thus freeing the wearer of the above-cited drawbacks. However, since the flaps are made of an opaque material, they remain visible, especially if the wearer is wearing skirts or a bathing costume such as a bathing suit or bikinis. This situation of potential discomfort in turn causes limited acceptance of this sanitary napkin by the market.

Therefore, until the present invention was made, women wearing bathing suits, sports clothes or skirts, would have to choose between a discreet sanitary napkin, but not providing due protection against leakage of menstrual flow, or a sanitary napkin that could protect but was not discreet, which would allow other people to notice that the woman was wearing it.

SUMMARY OF THE INVENTION

It is an objective of the present invention to provide a sanitary napkin that has good adherence and fixation to the undergarment of the wearer, while being discreet enough not to be noticed, even if the it is worn in conjunction with bathing suits, sports shorts, skirts or other women's garments.

In accordance with the present invention, there has been provided a sanitary napkin comprising a substantially planar and elongate main body having two longitudinally extending side edges. The main body includes a garment faceable outer layer of an impermeable material, a body faceable inner layer of a liquid permeable material and an absorbent core inserted into the body between the outer layer and the inner layer. The sanitary napkin further includes at least one substantially protuberant flexible flap, substantially projecting outwards from each longitudinal side edge of the main body of the sanitary napkin being wherein the flap portion is substantially transparent and/or translucent.

BRIEF DESCRIPTION OF THE DRAWINGS

The present invention will now be described in greater detail with reference to an embodiment represented in the drawings. The figures show.

DETAILED DESCRIPTION OF THE INVENTION

Figure 1:
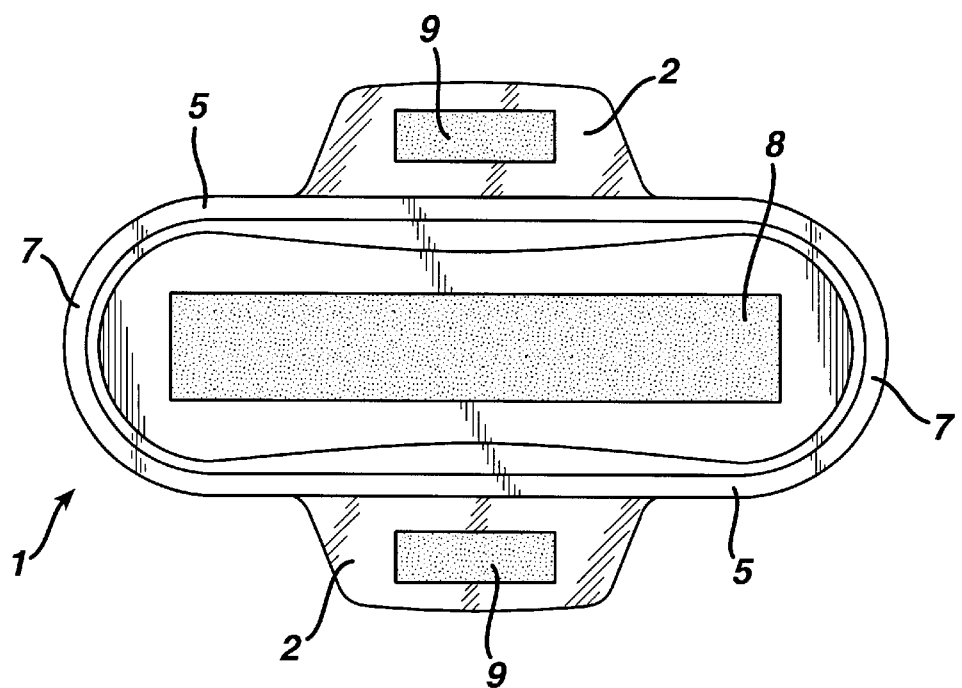
FIG. 1—a top view of the sanitary napkin of the present invention.
Figure 2:
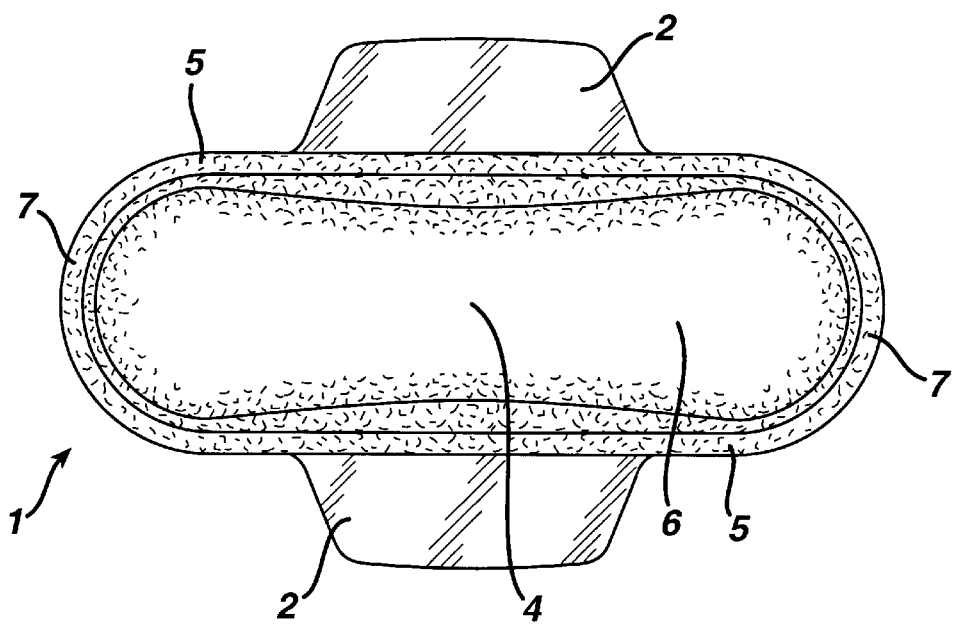
FIG. 2—a bottom view of the sanitary napkin of the present invention.

According to a preferred embodiment, and as can be seen from FIGS. 1–4, the sanitary napkin 1 of the present invention is composed of a substantially planar and elongate absorbent main body 4, having two longitudinal side edges 5, which are substantially rectilinear, and two transverse ends 7, which are substantially curvilinear, the center of curvature of each of the transverse ends 7 being substantially inside the region defined by the longitudinal side edges 5 and transverse ends 7. The main body 4 is made up of a liquid permeable cover layer, which is adapted to contact the wearer in use and to absorb any the menstrual flow that may be present. Under the liquid permeable cover layer is an absorbent element 3, which absorbs and retains the menstrual flow. Under the absorbent element 3 is a liquid impermeable outer layer, which prevents any absorbed liquids in the absorbent element 3 from leaking out of the sanitary napkin 1. The outer layer has a main adhesive layer 8, applied to its outer surface, which is adapted to contact the user's undergarment in use and to enable the user to releasably affix the sanitary napkin 1 to the undergarment. Before the sanitary napkin 1 is used, a release liner (not shown) covers the main adhesive layer 8.

The sanitary napkin 1 further comprises two flexible flaps 2, one flap projecting substantially laterally outward from each longitudinal side edge 5 of the body 4, respectively. Each flap 2 is substantially trapezoidal in shape, the larger side of the trapezoid being associated to the respective longitudinal side edge 5. Both flaps 2 are made of a transparent and/or translucent lucent material, In a preferred embodiment, each flap further having a secondary adhesive layer 9, just as was described above for the main adhesive layer 8, on a garment faceable surface of the flaps 2.

The present invention has as an advantage the fact that the thus-configured sanitary napkin presents fixation flaps that are transparent and/or translucent, thus being highly indicated to be worn together with bathing suits, sports shorts, skirts or other women's garments, having great resistance to displacement and movement, enabling the woman to wear it undisturbed, and it can be worn without other people noticing that the woman is wearing it, since the transparent and/or translucent flaps are unnoticeable one look from a certain distance.

In order to use the sanitary napkin 1, the release liner of the main adhesive layer 8 is removed and the sanitary napkin 1 is positioned over a crotch portion of the undergarment to releasably affix it therein. Next, the release liners are removed from the secondary adhesive layers 6 of the flaps 2, and both flaps 2 are folded over the edges of the crotch portion of the undergarment opposite the surface where the sanitary napkin 1 is positioned. In this way, the underwear is involved or "embraced", which enables the napkin 1 to be correctly fixed in position.

Figure 3:
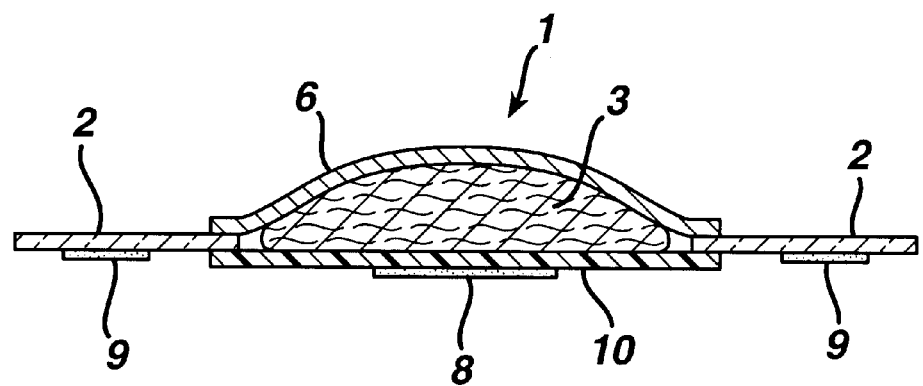
FIG. 3—a side cutaway view of a first embodiment of the sanitary napkin of the present invention.
Figure 4:
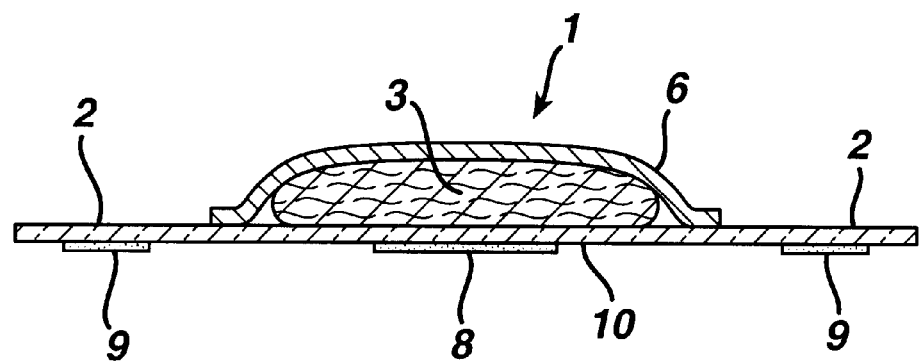
FIG. 4—a side cutaway view of a second embodiment of the sanitary napkin of the present invention.

As shown in FIG. 3. the side flaps 2 may be formed from a separate layer of a transparent and/or translucent flexible material and fixed to the body 4 of the sanitary napkin I during the process of producing the napkin 1. The separate layer of transparent and/or translucent flexible material may be affixed intermediate the cover layer and outer layer as shown in FIG. 3. Alternatively, the layer of transparent and/or translucent flexible material may be affixed to the cover layer on a body faceable surface of the napkin or to the outer layer on a garment faceable surface of the napkin. Optionally, however, one can provide a sanitary napkin I having the liquid impermeable outer layer made of a flexible, transparent and/or transparent and/or translucent flexible material lucent material as shown in FIG. 4. In this configuration, the flaps 2 are just continuous extensions of the liquid impermeable outer layer. Suitable transparent and/or translucent flexible materials include, but are not limited to, polymeric formed films such as polypropylene, polyethylene, and the like.

The sanitary napkin 1 and the flaps 2 may be formed with other shapes which are known in the art, as well as varying the number of flaps 2, without the present invention substantially differing from the preferred embodiment described herein.

A preferred embodiment having been described, one should understand that the scope of the invention includes other possible variations, and is limited only by the contents of the accompanying claims, the possible equivalents being included therein.

We claim:

1. A sanitary napkin adapted to be worn in a crotch portion of an undergarment in use, the sanitary napkin comprising a substantially planar and elongate main body having two longitudinal side edges, the main body having a garment faceable outer layer of a liquid impermeable material, a body faceable cover layer of a liquid permeable material, an absorbent core inserted into the main body between the outer layer and the inner layer, and at least one substantially protuberant flap portion, substantially projecting outwards from each longitudinal side edge of the main body of the sanitary napkin being wherein each flap is substantially transparent and/or translucent and wherein each flap is formed from a separate strip of material that is attached to the main body.

2. A sanitary napkin according to claim 1, wherein each flap has at least one adhesive layer applied to a garment faceable surface thereof.

* * * * *